(12) United States Patent
Kimoto

(10) Patent No.: US 8,088,534 B2
(45) Date of Patent: Jan. 3, 2012

(54) CHEMICALLY MODIFIED FULLERENE, PRODUCTION METHOD FOR THE SAME, AND PROTON CONDUCTING MEMBRANE INCLUDING THE SAME

(75) Inventor: Kyoji Kimoto, Kanagawa (JP)

(73) Assignee: Science Laboratories, Inc., Chiba (JP)

( * ) Notice: Subject to any disclaimer, the term of this patent is extended or adjusted under 35 U.S.C. 154(b) by 245 days.

(21) Appl. No.: 12/453,802

(22) Filed: May 22, 2009

(65) Prior Publication Data

US 2009/0297914 A1 Dec. 3, 2009

Related U.S. Application Data

(63) Continuation of application No. PCT/JP2007/073084, filed on Nov. 29, 2007.

(30) Foreign Application Priority Data

Nov. 30, 2006 (JP) ................................ 2006-323201

(51) Int. Cl.
*H01M 8/10* (2006.01)

(52) U.S. Cl. .......... 429/491; 429/492; 429/493; 521/27; 977/948

(58) Field of Classification Search .................. 429/491, 429/492, 493, 494, 483; 521/27, 28, 30; 977/948
See application file for complete search history.

(56) References Cited

U.S. PATENT DOCUMENTS

| 6,890,676 B2 | 5/2005 | Nuber et al. |
| 2005/0197467 A1 | 9/2005 | Komiya et al. |
| 2009/0004525 A1 | 1/2009 | Fukushima et al. |

FOREIGN PATENT DOCUMENTS

| JP | 2002-326984 A | | 11/2002 |
| JP | 2002326984 | * | 11/2002 |
| JP | 2003-303513 A | | 10/2003 |
| JP | 2005-68124 A | | 3/2005 |
| JP | 2005-93417 A | | 4/2005 |
| JP | 2005-251539 A | | 9/2005 |
| JP | 3984280 B1 | | 7/2007 |
| WO | WO-2004/112099 A2 | | 12/2004 |

OTHER PUBLICATIONS

Yamago et al., "Tertiary Phosphines, P-Chiral Phosphinites and Phosphonic Acid Esters Bearing Fullerene Substituent, Metal Complexes and Redox Properties", Tetrahedron, vol. 52, No. 14, pp. 5091-5102, Elsevier Science Ltd., 1996.
Isobe et al., "Synthesis of Hydrophosphorylated Fullerene under Neutral Conditions", Organic Letters, 2005, vol. 7, No. 25, pp. 5633-5635, American Chemical Society, Nov. 16, 2005.
Japan Office Action in corresponding Application 2006-323201, 3 pages, mailed on Mar. 12, 2007.
International Search Report mailed on Dec. 25, 2007.
International Preliminary Report on Patentability for application No. PCT/JP2007/073084 dated Jun. 11, 2009.
Kyoji Kimoto, "Development of PEFC Electrolyte Membrane", CMC Publishing Co., Ltd., p. 30 (Dec. 2005).

* cited by examiner

*Primary Examiner* — Raymond Alejandro
(74) *Attorney, Agent, or Firm* — Rader, Fishman & Grauer PLLC

(57) ABSTRACT

A chemical fullerene derivative is for a proton conducting membrane electrolyte, in which sulfonic acid group $SO_3M$ and/or phosphonic acid group $PO(OM)_2$ is directly bonded, but an organic compound is substantially not bonded. A production method is for the chemical fullerene derivative, which uses dimethylacetamide plus water in the case of sulfonation reagent $K_2SO_3$ and dioxane in the case of phosphonation reagent $LiPO(OEt)_2$.

4 Claims, 2 Drawing Sheets

CHEMICALLY MODIFIED FULLERENE, PRODUCTION METHOD FOR THE SAME, AND PROTON CONDUCTING MEMBRANE INCLUDING THE SAME

TECHNICAL FIELD

The present invention relates to chemically modified fullerene used for a proton conducting membrane in a polymer electrolyte fuel cell.

BACKGROUND ART

Conventionally, a perfluorinated sulfonic acid membrane (ex. Nafion (trademark) made by DuPont) is used as an electrolyte membrane, which determines the performance of the polymer electrolyte fuel cell. However, since it is expensive, hydrocarbon polymer based membrane has been studied in recent years. This kind of membrane has a structure of a sulfonic acid group directly bonded to an aromatic ring of the polymer. However, the performance of the membrane is deteriorated due to desulfonation reaction occurring gradually, as disclosed in Non-patent Reference 1, when it is used for a long period of time under acidic condition at 100 degrees Celsius or higher. Such a mechanism emanates from an electrophilic substitution reaction occurring due to proton attacking to the aromatic ring. Therefore, the development of a method of directly bonding the sulfonic acid group to a different substrate from the aromatic ring has been desired.

For such a purpose, a chemically modified fullerene made by directly bonding the sulfonic acid group to fullerene is disclosed in Patent Reference 1. However, it has a problem that a target substance cannot be obtained because dimethylformamide used as a reaction solvent is also bonded when a sulfonation reaction occurs. To solve this problem, Patent References 2 and 3 disclose methods of bonding the sulfonic acid group to fullerene via hydrocarbon or fluorinated spacer molecules. However, these methods have shortcomings such that they require a complex production system and that higher ion-exchange capacity cannot be provided.

Patent Reference 1: Japanese Unexamined Patent Application Publication No.2002-326984
Patent Reference 2: Japanese Unexamined Patent Application Publication No.2005-93417
Patent Reference 3: Japanese Unexamined Patent Application Publication No.2005-68124
Non-patent Reference 1: 'Development of PEFC electrolyte membrane', page 30, supervised by Kyoji Kimoto and published on December in 2005 by CMC Publishing Co., Ltd.

The inventor of this application has succeeded in directly bonding the sulfonic acid group to fullerene core without bonding of a reaction solvent by using $K_2SO_3$ as a sulfonation reagent and dimethylacetamide plus water as a specific reaction solvent. Meanwhile, phosphonated fullerene is generally disclosed in Patent Reference 2, however, a detailed preparing method is not disclosed, and the chemical structure of directly bonded type is not specified. The inventor of this application has used $LiPO(OEt)_2$ as a phosphonation reagent and dioxane as a preferable reaction solvent to successfully provide phosphonated fullerene of a direct bonding type. Since the phosphonic acid group is bivalent, it is useful to increase ion-exchange capacity and proton conductivity. Further, the chemically modified fullerene bearing either the sulfonic or phosphonic acid group is soluble in water. However, it should be water-insoluble when used as a proton conducting membrane electrolyte in a fuel cell. The phosphonic acid group is useful because it can be metal-bridged using polyvalent metal ions such as calcium or platinum ions to make the chemically modified fullerene water-insoluble.

DISCLOSURE OF THE INVENTION

To attain the above-mentioned objective, the present invention is chemically modified fullerene for a proton conducting membrane electrolyte with which sulfonic acid group $SO_3M$ and/or phosphonic acid group $PO(OM)_2$ is directly bonded but an organic compound is virtually not bonded (where M denotes an H or alkali metal ion). This chemically modified fullerene includes one to twelve of the following partial structure.

where X denotes $SO_3M$ or $PO(OM)_2$, and M denotes an H or alkali metal ion.

A production method for the aforementioned chemically modified fullerene, which uses dimethylacetamide plus water in the case of sulfonation reagent $K_2SO_3$, and dioxane in the case of phosphonation reagent $LiPO(OEt)_2$, is also the present invention. In the method, $K_2SO_3$ or $LiPO(OEt)_2$ is added to dispersed fullerene in the solvent, causing a reaction for 10 to 200 hours under normal or elevated pressure at 20 to 200 degrees Celsius,.

Further, a proton conducting membrane including the aforementioned chemically modified fullerene is also the present invention.

Furthermore, a proton conducting membrane in which a phosphonic acid group is metal ion bridged via polyvalent metal ions such as calcium or platinum ions is also the present invention.

RESULTS OF THE INVENTION

Using the chemically modified fullerene of the present invention, a proton conducting membrane, which prevents desulfonation reaction from occurring due to electrophilic substitution reaction brought about by proton attacking to the aromatic ring, can be produced. Further, desired water-insolubility can be easily provided using a metal ion bridge when the chemically modified fullerene is utilized for the proton conducting membrane. The chemically modified fullerene of the present invention may be used as a lithium battery electrolyte, solid acid catalyst to be used in biochemistry, and raw material to be used for medical materials or medicines.

BEST MODE FOR CARRYING OUT THE INVENTION

Figure 1:
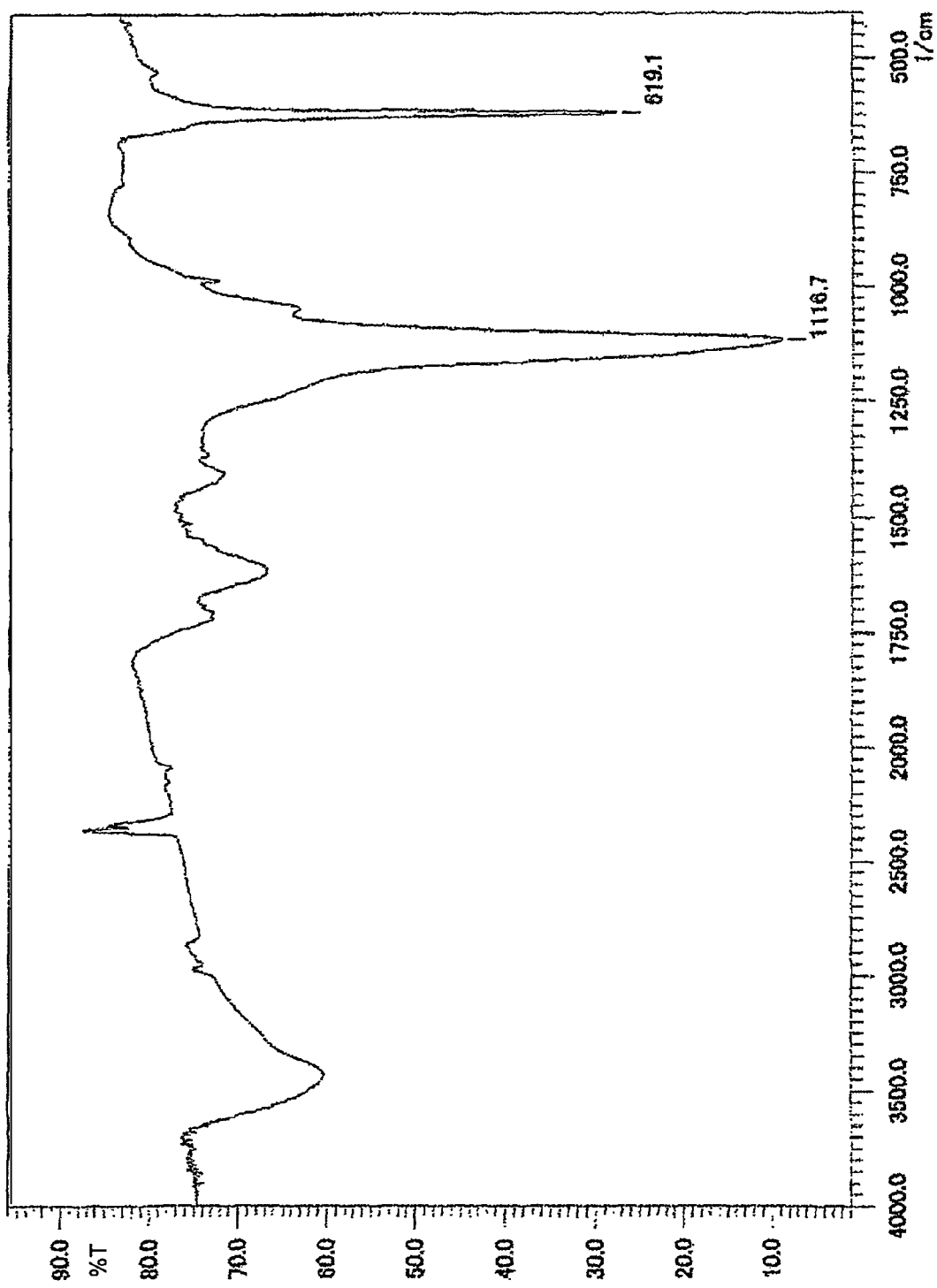
FIG. 1 shows an infrared absorption spectrum of chemically modified fullerene provided by a first example.

The present invention is chemically modified fullerene for a proton conducting membrane electrolyte with which sulfonic acid group $SO_3$ M and/or phosphonic acid group $PO(OM)_2$ is directly bonded but an organic compound is substantially not bonded (where M denotes an H or alkali metal ion). The total number of functional groups is normally between one and twelve, but it may be greater depending on the reaction conditions. The aforementioned chemically modified fullerene may be a chemically modified fullerene having practically the same number of functional groups, or it may be a mixture of chemically modified fullerenes differing in number of functional groups. The chemically modified fullerene of the present invention includes one to twelve of the following partial structure which is originated from the preparation reaction.

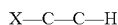

where X denotes $SO_3 M$ or $PO(OM)_2$, and M denotes H or an alkali metal ion.

The chemically modified fullerene according to the present invention may be produced by reacting fullerene such as C60, C70, C76, C78, or C84 as substrate with sulfonation reagent $K_2SO_3$ or phosphonation reagent $LiPO(OEt)_2$ in a specified organic solvent. This reaction is typically continued for 10 to 200 hours under normal or elevated pressure at 20 to 200 degrees Celsius.

The inventor's study has proved that, by measuring the infrared absorption spectrums of a product, reaction products of the fullerene and the sulfonation reagent are very different from each other depending on the type of organic solvent used. In the case of solvent bonding shown in the following table, an organic compound of a reaction solvent bonds to the fullerene, since complex peaks appear in the infrared absorption spectrum, allowing distinction from products having a simple peaks resulted from the target reaction. The chemical structure of DMF is $(CH_3)_2$ NCOH and that of DMAc is $(CH_3)_2$ NCOCH$_3$. Although they belong to the same amide solvent with very little difference in structure, reaction products are quite different from each other, which is an amazing discovery of the present invention.

TABLE 1

| Solvent used | DMF plus Water | DMAc plus water | Dioxane plus water | DMSO plus water |
|---|---|---|---|---|
| sulfonation reagent $K_2SO_3$ | solvent bonding | target reaction | no reaction | no reaction |
| sulfonation reagent NaSH | | solvent bonding | | |
| sulfonation reagent $KHSO_3$ | solvent bonding ※ | | | |

※ See the example of Patent Reference 1; the solvent is DMF.

One of the reasons why water is added to the organic solvent is to increase the solubility of sulfonation reagent in the organic solvent. The other reason is that an intermediate carbanion generated abstracts proton from water molecule before bonding to the solvent molecule, and then is stabilized as shown below.

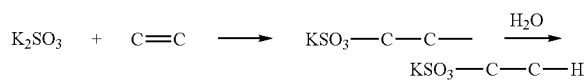

The $SO_3$ K type obtained by the reaction may be converted to either an $SO_3H$ type or another alkali metal ion type through ion exchange reaction.

A phosphonation reaction is described forthwith. Phosphonation reagent $LiPO(OEt)_2$ is prepared through the following reaction at 25 to 100 degrees Celsius using an aprotic organic solvent.

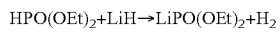

The fullerene is added thereto, causing a phosphonation reaction. In this reaction, dioxane is preferred organic solvent since solvent bonding occurs in the case of dimethylformamide. The difference of the reaction products can be investigated through infrared spectroscopy. In this case, tetrahydrofuran of the same cyclic ether may be used instead of dioxane. However, the boiling point thereof is low limiting the reaction temperature to be low resulting that dioxane is preferable organic solvent.

The intermediate carbanion generated in the phosphonation reaction abstracts proton from ethyl group of phosphonic acid ester or from dioxane of the solvent, and then stabilizes.

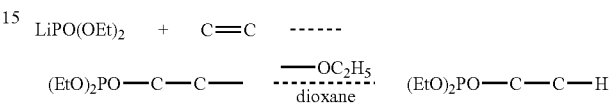

Proton of ethyl groups of phosphonic acid ester is easily abstracted through the following reaction, and is thus useful to prevent the intermediate carbanion generated from bonding to the solvent molecule.

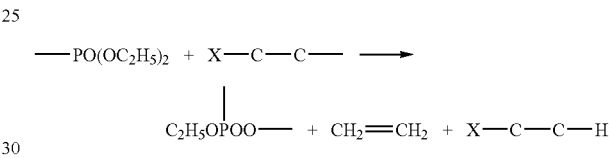

The phosphonic acid ester type provided through a phosphonation reaction may be converted to a phosphonic acid type $PO(OH)_2$ through hydrolysis by adding water after transesterification is made by reacting with trimethylsilyl bromide following a well known method. Further, the provided H type phosphonic acid group may be converted to an alkali metal ion type through ion exchange reaction, if necessary.

Furthermore, after the sulfonic acid group is introduced in the manner described above, the aforementioned phosphonation reaction may be conducted, thereby synthesizing the chemically modified fullerene bearing sulfonic acid groups coexisting with phosphonic acid groups.

According to the present invention, water is added for sulfonation reaction while diethyl phosphate is used for phosphonation reaction to stabilize the intermediate carbanion generated during the reaction prior to bonding to solvent molecules.

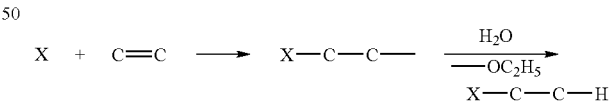

While the chemically modified fullerene of the present invention mainly includes the partial structure of a proton bonded at the β-position of X as described above, hydroxyl group OH or carboxyl group $CO_2H$ may be bonded in place of H in the partial structure as they are not organic compounds. Moreover, when the fullerene is bonded to two Xs, conjugated double bond is generated as shown in the following expression. Therefore, even if it includes a partial structure not bonded to a proton, it can be ignored because an organic compound is never be bonded thereto.

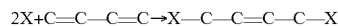

According to a method of manufacturing a proton conducting membrane of the present invention, a solution of perfluorinated sulfonic acid resin (ex. Nafion (trademark) resin made by DuPont) in lower alcohol plus water is mixed with the solution of the chemically modified fullerene of the present invention in either water or water plus lower alcohol, and the resulting solution is then applied to a reinforcing material such as a glass fiber nonwoven textile or a porous film of expanded polytetrafluoroethylene, thereby soaked thereinto, and then dried. According to the method described above, it is also possible to make a membrane using a solution of fluorinated resin, such as polyvinylidene difluoride, or the solution of hydrocarbon resin, such as polyethersulfone, polyetheretherketone, or polyimide in place of the perfluorinated sulfonic acid resin solution.

According to another method of manufacturing a proton conducting membrane of the present invention, the chemically modified fullerene of the present invention penetrates into a perfluorinated sulfonic acid membrane (ex. Nafion (trademark) membrane made by DuPont). In this case, the perfluorosulfonate membrane is soaked in the solution of the chemically modified fullerene of the present invention at 50 to 100 degrees Celsius for 10 to 100 hours. This allows the chemically modified fullerene of the present invention to penetrate into the perfluorosulfonate membrane.

The chemically modified fullerene of the present invention is soluble in water and may thus flow out while the proton conducting membrane is utilized in fuel cell. Therefore, in accordance with a well-known method, basic polymer electrolyte such as polybenzimidazole is added when making a membrane, thereby forming an ionic bridge between an acidic group and a basic group so that water-insolubility can be attained. However, according to the present invention, it is possible to add polyvalent metal ions such as calcium or platinum ions, thereby forming a metal ion bridge between phosphonic acid groups and resulting in providing water-insolubility. This process is easily carried out and is thus preferred. In the case of the chemically modified fullerene bearing a sulfonic acid group, by allowing the aforementioned coexistence of a phosphonic acid group, water-insolubility may be attained using the metal ion bridge.

Examples are described below; however, the present invention is not limited thereto.

FIRST EXAMPLE 720 mg fullerene C60 and 200 ml dimethylacetamide are put into a 300 ml three-necked flask. 790 mg potassium sulfite $K_2SO_3$ (five times that of fullerene in moles) is dissolved into 10 ml water and then added into the flask. Afterwards, the resulting solution is heated and stirred for four days at 80 degrees Celsius. Once the reaction is complete, the solvent is dried and removed, and the residue is extracted using ethanol. Solids are filtered out, and ethanol is then dried and removed from the filtrate. Afterwards, the infrared absorption spectrum is measured using KBr. The measurement shows a peak at 1117 cm$^{-1}$ representing $SO_2$ stretching and peak at 619 cm$^{-1}$ representing CS stretching (See FIG. 1). Further, S and K analysis is conducted using inductively coupled plasma atomic emission spectroscopy (ICP-AES), and element analysis of C, H, and O is conducted using a combustion method. These analyses show C: 57.5%, S: 11.4%, K: 14.7%, H: 0.55%, and 0: 13.0% indicating that four to five elements of H and sulfonic acid group $SP_3K$ are bonded together. Furthermore, a sample is dissolved in $D_2O$ and NMR is then measured. This shows a peak presumably representing a β-positioned proton. Yield of the obtained sulfonated fullerene is 30% on a fullerene basis.

COMPARATIVE EXAMPLE

Figure 2:
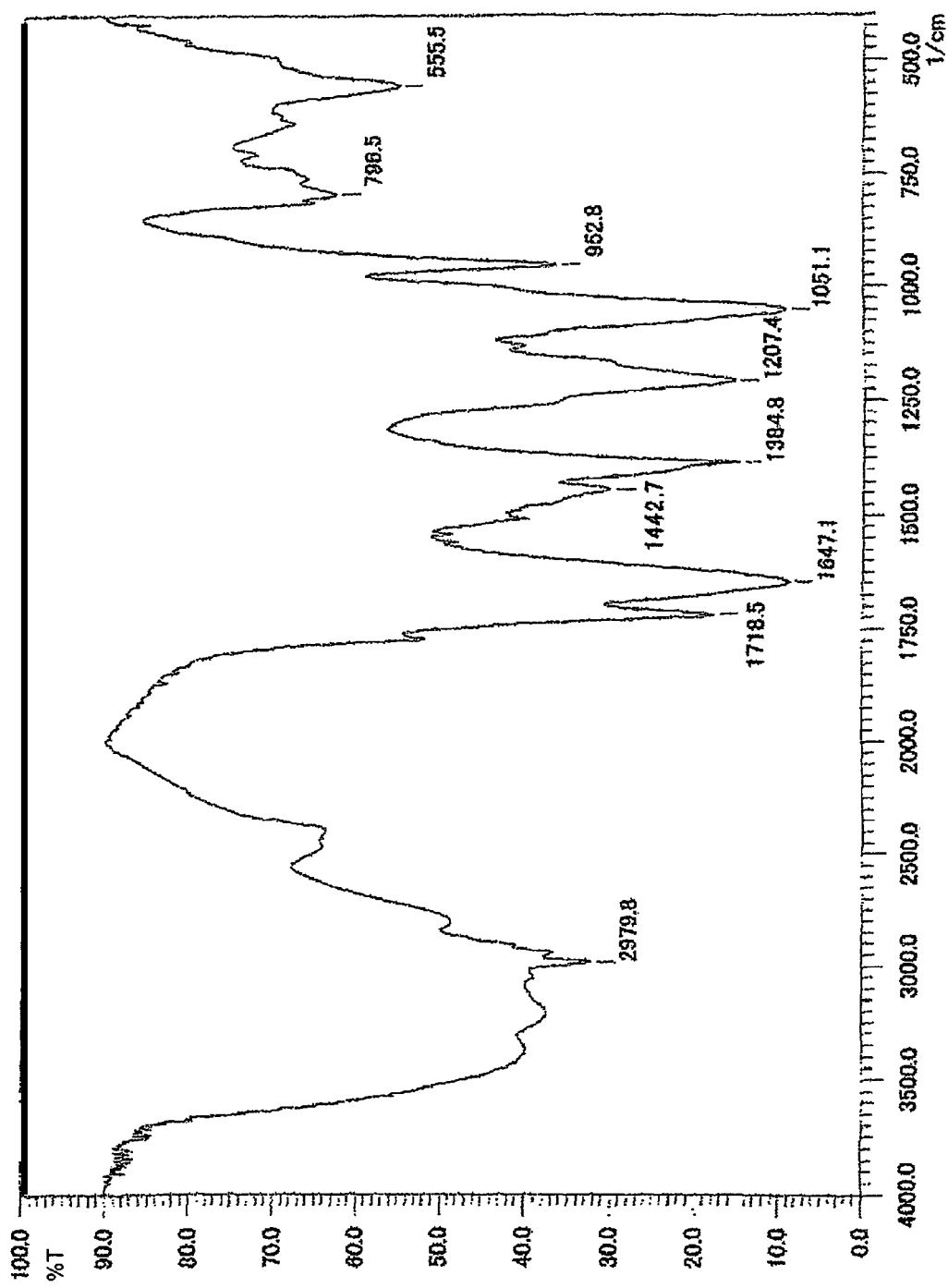
FIG. 2 shows an infrared absorption spectrum of chemically modified fullerene provided in a comparative example.

Dimethylformamide is used in place of dimethylacetamide used in the first example and the same processing as that of the first example is conducted, measuring the infrared absorption spectrum of the resulting product. This measurement shows lots of peaks indicating that dimethylformamide used as solvent molecule is bonded (See FIG. 2).

SECOND EXAMPLE 690 mg diethyl phosphate $HPO(OEt)_2$ and 200 ml dioxane are put into a 300 ml three-necked flask, and then 40 mg LiH is added thereto. It is then heated and stirred at 80 degrees Celsius, resulting in generation of $H_2$. Shortly thereafter, the solution becomes transparent. At this time, 720 mg fullerene C60 is added thereto, and the resulting solution is heated and stirred for four days at 80 degrees Celsius. After the reaction is completed, the solvent is dried and removed. The residue is then extracted using ethanol plus THF, and solids are filtered out. The ethanol plus THF is then dried and removed from the resulting filtrate. Afterwards, the infrared absorption spectrum is measured using KBr, showing absorption of $C_2H_5$ at 2926 cm$^{-1}$, absorption of P=O at 1209 cm$^{-1}$, and absorption of P—O—C at 1043 cm$^{-1}$, which has proved that phosphonic ester group $PO(OEt)_2$ is bonded. 1 g trimethylsilyl bromide is added to this 500 mg phosphonated fullerene, and transesterification is conducted overnight at room temperature. Afterwards, hydrolysis is conducted by adding water thereto. The resulting product is then dried and measured in infrared absorption spectrum using KBr. This measurement shows that there is no absorption of $C_2H_5$ but absorption of OH at 3348 cm$^{-1}$, absorption of P=O at 1184 cm$^{-1}$, and absorption of P—O—C at 1074 cm$^{-1}$. The obtained phosphonated fullerene is subjected to P analysis using ICP-AES and also element analysis for C, H, and O using a combustion method. The analyses show C: 73.9%, P: 10.6%, H: 1.4%, and O: 15.5% indicating that three to four elements of H and phosphonic acid group $PO(OH)_2$ are bonded together. Further, a sample is dissolved in $D_2O$ and NMR is measured. This measurement shows a peak presumably representing β-positioned proton. Yield of the obtained phosphonated fullerene is approximately 35% on a fullerene basis.

THIRD EXAMPLE

The same processing as that of the second example is conducted using the sulfonated fullerene provided in the first example as a raw material. As a result, absorption peaks of a sulfonic acid group and a phosphonic acid group appear in the infrared absorption spectrum indicating the coexistence of them.

FOURTH EXAMPLE

A 20 g solution containing 5% Nafion (trademark) resin in (PrOH+Water) (made by Aldrich Corporation; EW=1100) is put in a 50 ml beaker. A solution made by dissolving the 500 mg phosphonated fullerene from the second example in 5 ml water is then added thereto. A solution made by dissolving 10 mg calcium chloride in 5 ml water is added thereto and then stirred for 30 minutes using a homogenizer. The obtained dispersion liquid is applied to a 100 μm glass fiber nonwoven textile (made by Japan Vilene Company, Ltd.) using a brush, penetrated into vacancies thereof. This processing is repeated ten times. Afterwards, it is dried at 100 degrees Celsius, resulting in a proton conducting membrane. The membrane is then immersed in water overnight. Afterwards, changes in P content value are measured using ICP-AES. However, no difference between before and after immersion is detected indicating that no phosphonated fullerene is eluted out.

What is claimed is:

1. A chemical fullerene derivative for a proton conducting membrane electrolyte that comprises:
   a sulfonic acid group $SO_3M$ or phosphonic acid group $PO(OM)_2$ that is directly bonded, but any organic compound that is not bonded, wherein M denotes either an H or alkali metal ion;
   said chemical fullerene derivative further comprising one to twelve of the following partial structure:

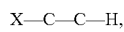

wherein X denotes either $SO_3M$ or $PO(OM)_2$, and M denotes either an H or alkali metal ion.

2. A proton conducting membrane, comprising the chemical fullerene derivative according to claim 1.

3. The proton conducting membrane according to claim 2, in which phosphonic acid groups are metal ion bridged via polyvalent metal ions such as calcium ions or platinum ions.

4. A production method for the chemical fullerene derivative according to claim 1, said production method comprising steps of:
   using dimethylacetamide plus water as a solvent in the case of sulfonation reagent $K_2SO_3$, or using dioxane as a solvent in the case of phosphonation reagent $LiPO(OEt)_2$; and
   dispersing fullerene, $K_2SO_3$ or $LiPO(OEt)_2$ in the solvent, causing a reaction for 10 to 200 hours under a normal or elevated pressure at 20 to 200 degrees Celsius.

* * * * *